(12) United States Patent
Liang et al.

(10) Patent No.: US 10,201,378 B2
(45) Date of Patent: Feb. 12, 2019

(54) INJECTION DEVICE FOR BIOLOGICAL TISSUE REPAIR

(71) Applicant: WILTROM CO., LTD., Hsinchu County (TW)

(72) Inventors: Huang-Chien Liang, Hsinchu (TW); Chun-Jen Liao, Taipei (TW); Yu-Ming Wang, Tainan (TW); Hung-Yin Tai, Hsinchu (TW); Shih-Chang Chuang, Taichung (TW); Yung-Fang Tsai, Taichung (TW)

(73) Assignee: Wiltrom Co., Ltd., Hsinchu County (TW)

( * ) Notice: Subject to any disclaimer, the term of this patent is extended or adjusted under 35 U.S.C. 154(b) by 371 days.

(21) Appl. No.: 15/077,007

(22) Filed: Mar. 22, 2016

(65) Prior Publication Data

US 2016/0278835 A1  Sep. 29, 2016

Related U.S. Application Data

(60) Provisional application No. 62/136,708, filed on Mar. 23, 2015.

(51) Int. Cl.
| | |
|---|---|
| *A61B 17/88* | (2006.01) |
| *B01F 7/00* | (2006.01) |
| *B01F 13/00* | (2006.01) |
| *B01F 15/02* | (2006.01) |
| *B01F 15/06* | (2006.01) |
| *A61B 17/00* | (2006.01) |
| *A61B 90/00* | (2016.01) |

(52) U.S. Cl.
CPC ...... *A61B 17/8822* (2013.01); *A61B 17/8819* (2013.01); *A61B 17/8825* (2013.01); *A61B 17/8836* (2013.01); *B01F 7/00416* (2013.01); *B01F 13/0027* (2013.01); *B01F 15/0237* (2013.01); *B01F 15/068* (2013.01); *A61B 2017/00685* (2013.01); *A61B 2017/8838* (2013.01); *A61B 2090/031* (2016.02); *B01F 2015/062* (2013.01)

(58) Field of Classification Search
CPC ............... B01F 7/0045; B01F 7/00416; A61B 17/8822; A61B 17/8819; A61B 17/8825; A61B 17/8836
USPC ...................................... 606/92–95
See application file for complete search history.

(56) References Cited

U.S. PATENT DOCUMENTS

| | | | |
|---|---|---|---|
| 6,033,105 | A | 3/2000 | Barker et al. |
| 8,603,096 | B2 | 12/2013 | Agard et al. |
| 2004/0030345 | A1 | 2/2004 | Aurin et al. |

(Continued)

FOREIGN PATENT DOCUMENTS

TW    201422268 A    6/2014

*Primary Examiner* — Matthew J Lawson
(74) *Attorney, Agent, or Firm* — Rosenberg, Klein & Lee

(57) ABSTRACT

An injection device is provided for repairing biological tissues and comprises a body, a chamber, an exterior tube, and a screw rod. The chamber is connected with the body and used for accommodating a repairing material. The exterior tube is connected with the chamber. The screw rod is disposed inside the chamber and the exterior tube. The threads of the screw rod disperse the repairing material. By using the threads of the screw rod and a driving force originating from the end of the screw rod, the repairing material is delivered into an organism.

22 Claims, 7 Drawing Sheets

(56) References Cited

U.S. PATENT DOCUMENTS

| | | | |
|---|---|---|---|
| 2005/0245938 A1* | 11/2005 | Kochan | A61B 17/7097 606/92 |
| 2006/0149282 A1* | 7/2006 | Vendrely | A61B 5/03 606/94 |
| 2007/0118144 A1* | 5/2007 | Truckai | A61B 17/8811 606/93 |
| 2008/0027456 A1* | 1/2008 | Truckai | A61B 17/8811 606/94 |
| 2010/0211058 A1* | 8/2010 | Winterbottom | A61B 17/8836 606/29 |
| 2010/0262152 A1* | 10/2010 | Shadduck | A61B 17/8822 606/94 |
| 2011/0028980 A1 | 2/2011 | Click et al. | |
| 2011/0137318 A1* | 6/2011 | Liao | A61B 17/8822 606/93 |
| 2012/0259213 A1* | 10/2012 | Conquergood | A61B 17/320016 600/431 |
| 2013/0079786 A1 | 3/2013 | Bonnin et al. | |
| 2013/0190680 A1* | 7/2013 | Baroud | A61B 17/8811 604/28 |
| 2013/0269671 A1 | 10/2013 | Tseng | |
| 2013/0289571 A1 | 10/2013 | Click et al. | |
| 2014/0005703 A1* | 1/2014 | Stulen | A61B 17/29 606/169 |
| 2014/0163567 A1 | 6/2014 | Lin et al. | |
| 2017/0128113 A1* | 5/2017 | Vogt | A61B 17/8819 |

* cited by examiner

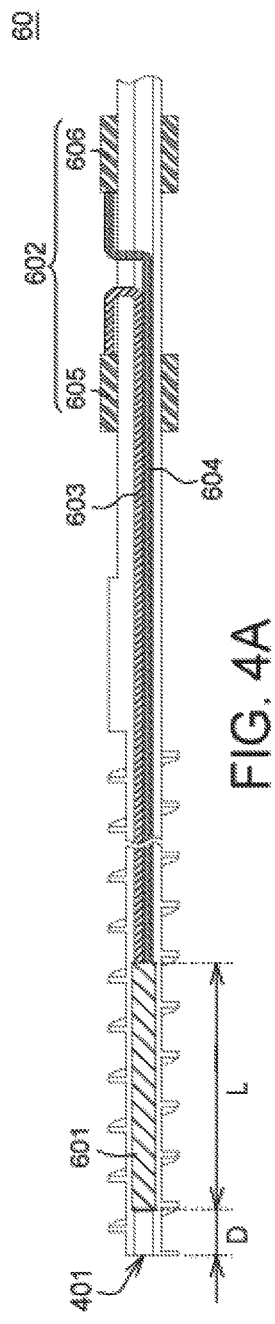
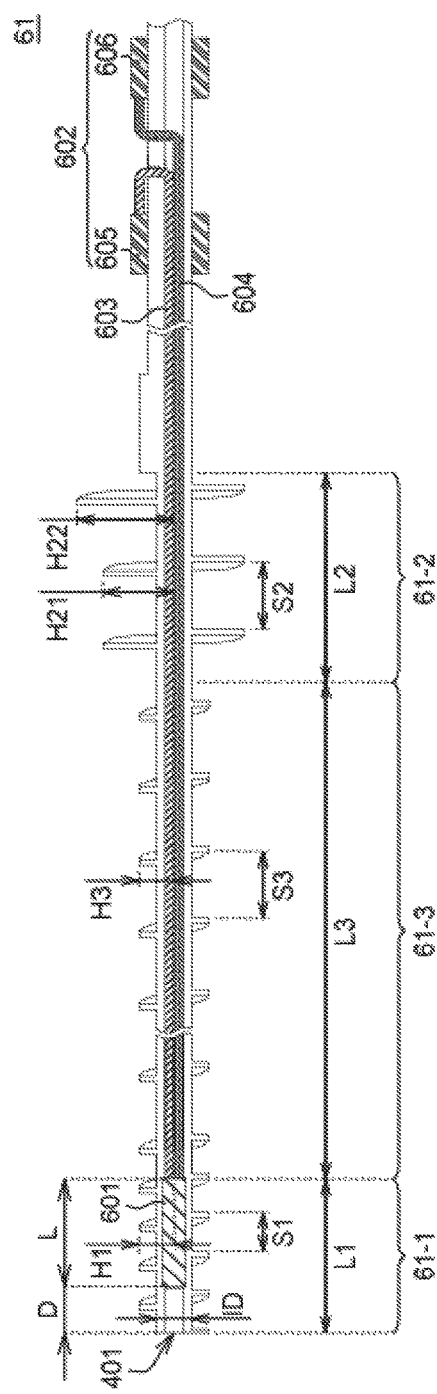
FIG. 4A
FIG. 4B

INJECTION DEVICE FOR BIOLOGICAL TISSUE REPAIR

The present invention relates generally to an injection device, and particularly to an injection device for repairing biological tissues.

REFERENCE TO RELATED APPLICATION

This Application is being filed based on Provisional Application Ser. No. 62/136,708, filed 23 Mar. 2015, currently pending.

BACKGROUND OF THE INVENTION

Recently, repairing materials, like bone cement, become increasingly important in bone treatment. In particular, the treatment methods applied in vertebral support and vertebroplasty for preventing compression on spinal cord can further replace traditional nerve decompression operations or combine with traditional spinal fixation operations to solve nerve compression. In addition to higher patient acceptance, this treatment method is further applied extensively to treating compressive fracture due to various primary and secondary osteoporosis and reinforcing vertebral stability.

The minimally invasive surgery of vertebroplasty is performed in vertebral columns using percutaneous puncture technique. By introducing repairing materials into damaged vertebral columns, the strength of the vertebral columns and vertebral stability can be enhanced. Besides, patients' chronic pains caused by the damaged vertebral columns can be reduced as well. The Poly-methyl methacrylate (PMMA) is the mainly adopted as the repairing materials.

In order to inject repairing materials into damaged vertebral columns, the injection devices for repairing materials become extremely important. The stability of injection rate, the convenience in applying force, and the adaptation to other devices impose direct influences on the efficacy of injection devices. They also determine indirectly the success of surgery outcomes. Currently, the majority of injection devices for repairing materials are syringes. A repairing material is placed in a syringe having a special injection needle disposed at the injection passage. Then, like normal injections, the piston is used to compress and inject the repairing material inside the syringe into the target bone through the specially designed injection needle. Nonetheless, in the injection method, the resistance of pushing and compressing the piston will become increasingly greater because the repairing material will coagulate gradually during the injection process. Under the circumstance, it is difficult to inject the repairing material; the injection rate will change from fast to slow. Then the injected repairing material is fewer than expected and thus affecting the efficacy of the surgery.

Recently, the adopted repairing materials with thermoplastic are commonly used in biological tissue repair as well, which means that the repairing materials are softened and transformed to be fluid by heating and become plastic. After cooling, they recover to be solid and thus reinforcing the strength and stability of vertebral columns. The molecular chains of this type of material are mostly linear or structures having sub-chains. Thereby, by physical changes, the materials can be softened by heating and hardened by cooling. In particular, poly(D, L-lactic-co-glycolic) acid (PLGA) is the mainly adopted as the repairing materials with thermoplastic.

Furthermore, in order to place repairing materials into damaged vertebral columns successfully, according to the existing techniques, the bone material to be injected should be molten completely. Then the molten repairing material should be loaded into the injection device before the repairing material is injected into bones for reinforcing the bone structure. Nonetheless, by using this method, heating the repairing material at relatively higher temperatures and longer time might damage the repairing material. Besides, because the repairing material starts to coagulate shortly after it is molten completely, the imposed time limit in the process from melting to injection will be totally depend on material properties. This time limit results in lower adaptability in a surgery process that might vary from minute to minute. Consequently, this will bring inconvenience for doctors in surgeries and hence affecting surgery outcome.

Accordingly, how to design an injection device having the properties of convenient operations, stable injection rates, and real-time heating capability for repairing materials has become a major subject in the field.

SUMMARY

An objective of the present invention is to provide an injection device. By using the structure design, repairing materials can be delivered to the exterior tube of the injection device with ease. In addition, no excessively high heating temperature and long heating time are required for injecting repairing materials into a human body. In addition to saving resources, the efficiency of surgeries can be enhanced effectively.

Another objective of the present invention is to provide an injection device. By using the structure design, repairing materials are heated and transformed inside the injection device and then injected immediately. Thereby, repairing materials can be refilled promptly according to the requirement of a surgery. It is no need to consider the coagulation time of repairing materials. Hence, the usage flexibility in a surgery is improved.

A further objective of the present invention is to provide an injection device. By using the structure design, a stable rotational force is provided to the screw rod of the injection device. By converting the rotational force to linear delivery, repairing materials cab be delivered stably and hence increasing surgery stability.

In order to achieve the above objectives, the present invention provides an injection device, which comprises a body, a chamber, an exterior tube, and a screw rod. The chamber is connected with the body and used for accommodating a repairing material. The exterior tube is connected with the chamber and includes an outlet at one end. The screw rod is disposed inside the chamber and the exterior tube. The threads of the screw rod disperse the repairing material. By using the threads of the screw rod and a driving force originating from the end of the screw rod, the repairing material is delivered and output.

BRIEF DESCRIPTION OF THE DRAWINGS

FIG. 4A shows a partially enlarged view of the screw rod according an embodiment of the present invention;

FIG. 4B shows a partially enlarged view of the screw rod according to another embodiment of the present invention;

DETAILED DESCRIPTION

In order to make the structure and characteristics as well as the effectiveness of the present invention to be further understood and recognized, the detailed description of the present invention is provided as follows along with embodiments and accompanying figures.

Currently, bone repairing materials should be molten first before they can be loaded to an injection device for delivery. In addition, by using an injection device, the injection rate might be unstable owing to gradual coagulation of repairing materials during the injection process. Hence, the present invention provides a novel injection device. According to the present invention, a heater is designed in the exterior tube. Thereby, the high-temperature and long-time heating process for melting repairing materials completely can be avoided and thus preventing changes in the physical properties of the repairing materials. In addition, by using this design, because repairing materials are heated and transformed inside the injection device and then injected immediately, they can be refilled at any time, depending on the requirements of a surgery. It is not necessary to consider the coagulation time of repairing materials and hence improving flexibility in surgery applications. Furthermore, by using the screw rod design inside the exterior tube, the rotational force can be converted to linear motions for delivery. By operating in coordination with a driving device that can provide stable spinning rates, stable delivery can be achieved.

Accordingly, the present invention provides an injection device. A powdered repairing material is disposed in a chamber. A piston and a screw rod, which are moved dependently by a driving device, are disposed inside the chamber. The powdered repairing material is brought away the chamber and into the exterior tube by the screw rod through spiral rotations. By using the driving device to drive the screw rod to spin, a stable and controllable delivery method is provided. Next, the repairing material is heated by the heating zone and then molten and transformed. Finally, the molten and transformed repairing material is injected through an outlet at one end of the exterior tube. By using the above steps, the repairing material can be delivered to the exterior tube of the injection device with ease. No excessively high heating temperature and long time is required. Besides, because the repairing material is injected right after it is heated and transformed in the injection device, the repairing material can be refilled at any time in a surgery.

Based on the above description, in the following, the components, properties, assembling method, and the mechanism of the injection device according to the present invention will be described.

Figure 1:
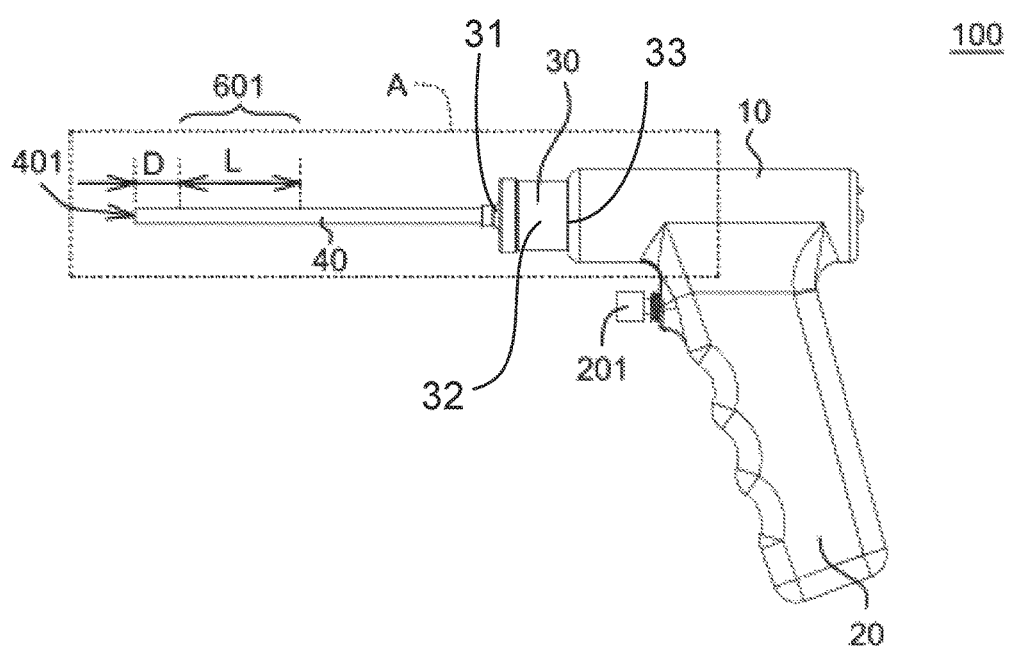
FIG. 1 shows a schematic diagram of the injection device according an embodiment of the present invention.
Figure 2A:
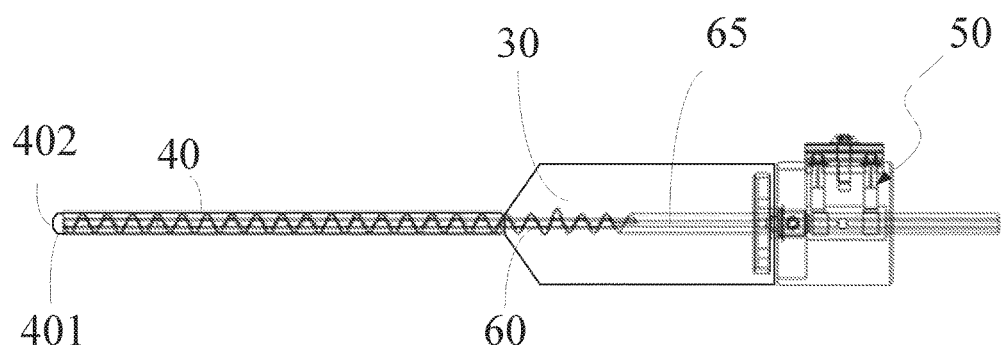
FIGS. 2A to 2D show perspective views of the region A of the embodiment in FIG. 1.

Please refer to FIG. 1 and FIG. 2A, which show a schematic diagram of the injection device according an embodiment of the present invention and a perspective view of the region A in FIG. 1. As shown in the figures, the present invention provides an injection device, which comprises a body 10, a chamber 30, an exterior tube 40, and a screw rod 60. The chamber 30 is used for accommodating a power repairing material, and includes a first opening 31 at the front end, an internal space 32, and a second opening 33 at the rear end. The screw rod 60 is disposed in the internal space 32. The screw rod 60 extends through the first opening 31 connected with the exterior tube 40 and is disposed inside the exterior tube 40. In addition, the chamber 30 is connected with the body 10 through the second opening 33. From the inside of the body 10, a driving force is delivered to the screw rod 60, which includes a spinning shaft 65 at one end. The spinning shaft 65 is driven by the driving force and then driving the screw rod 60. Thereby, the disposition for driving the present invention is finished.

The first opening 31 of the chamber 30 is connected with the exterior tube 40 by tight joining or soldering for ensuring that the power repairing material will not leak during the delivery process from the chamber 30 to the exterior tube 40.

In addition, the second opening 33 of the chamber 30 and the body 10 are connected in a detachable manner. By using the design, the chamber 30 can be detached from the body 10. After refilling the power repairing material, it can be reattached to the body 10. Based on the above property, according to a preferred embodiment, the second opening 33 of the chamber 30 and the body 10 are connected by screwing or wedging. According to another embodiment, the chamber 30 can include an inlet for filling repairing materials and a cover (not shown in the figures). The purpose of filling repairing materials in the chamber 30 can be achieved as well.

Moreover, the exterior tube can further include a narrowed outlet 402 at the outlet 401. The inner diameter of the narrowed outlet 402 is smaller than the inner diameters of the exterior tube 40 and the outlet 401. By using the design, when a repairing material is delivered to the narrowed outlet 402 by the rotation of the screw rod 60, the repairing material can be output in a column shape, which facilitates easier operations of tools. According to an embodiment, the inner diameter of the exterior tube 40 can be less than 6 millimeters. Nonetheless, the present invention is not limited to the length.

Please refer again to FIG. 2. The perspective views describe the operations of the injection device provided by the present invention. When a user puts a repairing material into the chamber 30, the driving force provided by the body 10 can be used to rotate the spinning shaft 65 and the screw rod 60. The repairing material can be carried in the screw rod 60. When the screw rod 60 rotates, the threads of the screw rod 60 can deliver and disperse the repairing material. By using the threads of the screw rod 60 and the driving force, the repairing material can be delivered from the chamber 30 through the exterior tube 40 and to the outlet 401 of the exterior tube 40 for outputting. By the mechanism of the injection device according to the present invention, the rotating motion is converted to linear motion by the screw rod 60. By using the smaller spinning force to gain a greater forward force. Thereby, the repairing material can be transported continuously and stably. As the screw rod rotates, the repairing material will attach to the spiral curved surfaces of the screw rod 60 and move. In this way, the friction between the repairing material and the inner sidewall of the exterior tube 40 can be reduced. Hence, even the injection location is deeper, the screw rod 60 still can transport the repairing material to the affected part. In addition, as the repairing material in the chamber 30 enters the screw rod 60 continuously, uninterrupted injection can be performed at the front end.

The embodiments of the repairing materials according to the present invention include power, granular, or sticky repairing materials. When the repairing material is powdered or granular, according to a preferred embodiment, the particle size can be, but not limited, between 10 µm and 3 millimeters. In addition, the gradients of the repairing materials provided by the present invention can be selected from the group consisting of thermoplastic biologically-compatible polymers and a calcium biologically-compatible salt. The thermoplastic biologically-compatible polymers can include poly(glycolic acid), poly(L-lactic acid), poly(D, L-lactic acid), poly(D, L-lactic-co-glycolic) acid (PLGA), or polycaprolactone. The calcium biologically-compatible salt can include hydroxyapatite, tricalcium phosphate, calcium sulfate, dicalcium pyrophosphate, or tetracalcium phosphate. Nonetheless, the present invention is not limited to the above. According to a preferred embodiment, the gradients of the repairing material are prepared by mixing poly(D, L-lactic acid) and tricalcium phosphate. In addition, the amount of the repairing material can be adjusted according to the sizes of the chamber 30, the exterior tube 40, and the screw rod 60. Because powdered or granular repairing materials accumulate easily, their movement in the injection device according to the present invention is not smooth. Thereby, introducing the design of the threads of the screw rod 60 in the injection device facilitates dispersing and moving the repairing materials.

Figure 2B:
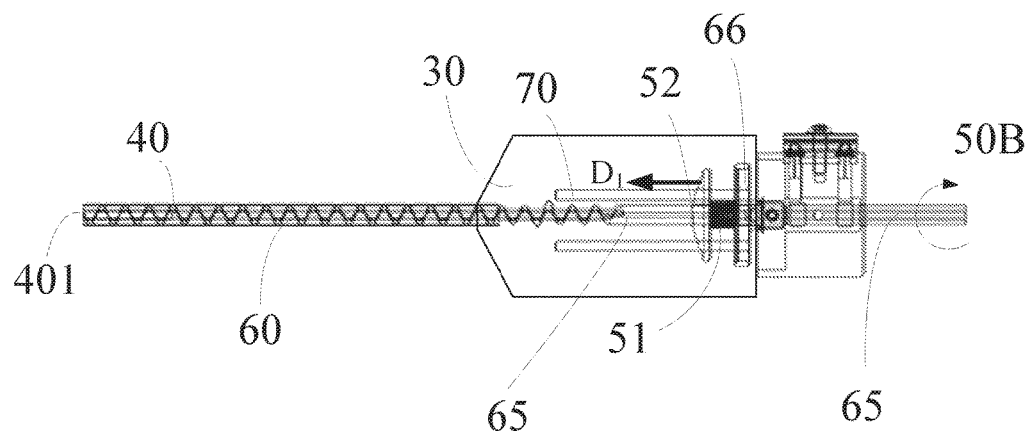

As shown in FIG. 2A, the injection device according to the present invention comprises a driving device 50 used for providing the driving force. The driving device 50 includes a motor and related components (such as circuit boards and batteries). According to an embodiment, the motor (and the circuit boards and batteries) are disposed in the body 10 for providing the injection device with a strong and stable driving force. Then the repairing material can be carried by the screw rod 60 and delivered to the exterior tube 40 and the outlet 401 by the spinning force. Besides, the motor of the driving device 50 can be disposed outside the body 10. As shown in FIG. 2B, the driving force inside the body 10 comes from a motor 50 (such as an external electric drill) outside the body 10 and is used for delivering the repairing material.

Please refer again to FIG. 1. As shown in the figure, the injection device can further comprise a holding part 20 connected with the body 10. The holding part 20 includes a motor switch 201 connected with the driving device 50. The inside of the holding part 20 can used for disposing the motor (or the components including the circuit boards and batteries providing the driving force) of the driving device, and thus simplifying the internal space of the body 10. When the user holds the holding part 20, he can press the motor switch 201 with his index finder easily. Then the internal components such as the motor can generate a driving force, which is delivered to the end of the screw rod 60 inside the chamber 30 and injects the repairing material. According to another preferred embodiment, the injection device can also be connected to an AC power source for saving the internal space of the holding part 20.

In addition, a power switch and a power indicator (not shown in the figure) can be included to the outside of the body 10. When the power switch is turned on, the power indicator will be lit up. As the power indicator is put out, the motor switch 201 will be electrically active. At this time, the motor switch 201 can be pressed to rotate the motor and thus driving the screw rod 60 to spin and carry the powdered or granular repairing material out of the chamber 30.

Please refer again to FIG. 1. As shown in the figure, the injection device can further comprise a heating part 601, which defines a zone length L and a distance D to the outlet 401. The heating part 601 can be disposed inside the exterior tube 40, inside the chamber 30, or inside both. The heating part 601 is disposed in the zone and heat the repairing material. Then the powdered repairing material can be molten and transformed and hence be moved by the screw rod 60 to the outlet 401 in the molten form. Thereby, the repairing material can be output and meet the requirements of repairing bone tissues. According to a preferred embodiment, the injection device according to the present invention can further comprise a heat insulating part (not shown in the figure) between the exterior tube 40 and the screw rod 60. The heat insulating part can, for example, be attached to the inner or outer sidewall of the exterior tube 40 for preventing the heat generated by the heating part 601 from delivering outwards.

Please refer to FIG. 2B. According to a preferred embodiment, in or to apply the kinetic energy of the driving device 50 to the repairing material more effectively, the driving device 50 according to the present invention can further include a spring 51 and a push-and-block member 52 disposed inside the chamber 30 and a segment of the spinning shaft 65 of the screw rod 60 and attached to a driving sleeve 66 located at the interface between the body 10 and the chamber 30. The diameter of the penetrating hole of the push-and block member 52 is slightly greater than the inner diameter of the spinning shaft 65, so that the push-and block member 52 is movable along the spinning shaft 65. When the repairing material inside the chamber is plenty, it will compress the spring 51 and the push-and block member 52. As the driving device 50 drives the screw rod 60 and deliver the repairing material to the exterior tube 40, the compressing force applied by the repairing material on the spring 51 and the push-and block member 52 will decrease. At this time, the spring 51 will press the push-and block member 52, which, in turn, will press the repairing material. Then a pushing force in the label D1 direction in FIG. 2B will be generated. Then the accommodating space in the chamber 30 will shrink, and hence generating pressure on the repairing material and delivering the repairing material to the exterior tube 40.

Figure 2C:
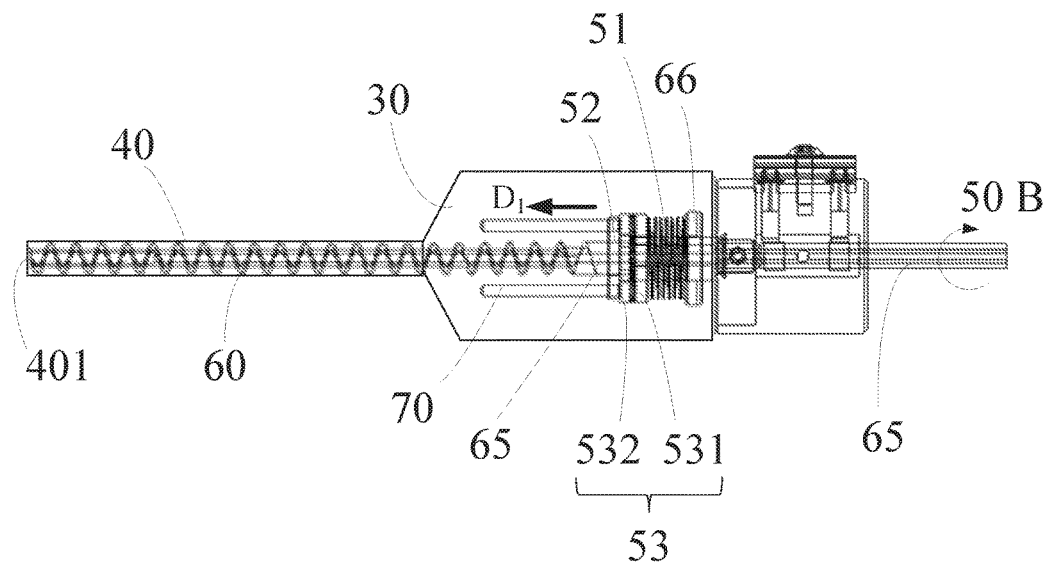

Please refer to FIG. 2C. According to a preferred embodiment, in order to avoid excessively tight accumulation of the repairing material at the junction of the chamber 30 and the exterior tube 40 during the process of the pushing force D1 delivering the repairing material to the exterior tube 40, which can disable the screw rod 60 from delivering the repairing material to the exterior tube 40, the driving device 50 according to the present invention can further include a clutch 53 disposed at the segment of the spinning shaft 65 of the screw rod 60 and located between the spring 51 and the push-and-block member 52. The clutch 53 includes a transmission lid 531 and a transmission plate 532. The transmission lid 531 is attached tightly to the spring 51. When the driving device 50 provides a driving force, the transmission lid 531 will spin along with the spinning shaft 65. Besides, the transmission plate 532 is attached to the push-and-block member 52 but does not move with the spinning shaft 65. As the repairing material inside the chamber 30 is loose, the spring 51 will push the transmission lid 531 and the transmission plate 532 to combine closely. At this time, the driving force given by the spinning shaft 65 will be delivered axially to the transmission plate 532 and the push-and-block member 52 via the transmission lid 531 and compressing the repairing material. On the other hand, once the repairing material inside the chamber 30 is too tight, the friction generated by the accumulation of the repairing material will be greater than the force applied by the spring 51 on the transmission lid 531. Then the transmission lid 531 will rotate with respect to the transmission plate 532, instead of rotating as a whole (just like the clutch effect). The transmission lid 531 will not rotate and the repairing material will not be pushed forward. At this time, the screw rod 60 will continue to deliver the repairing material to the exterior tube 40 until the friction generated by the accumulation of the repairing material will be smaller than the force applied by the spring 51 on the transmission lid 531. Then the transmission lid 531 will redeliver a driving force to the transmission plate 532 and the push-and-block member 52 for pushing the repairing material.

Figure 2D:
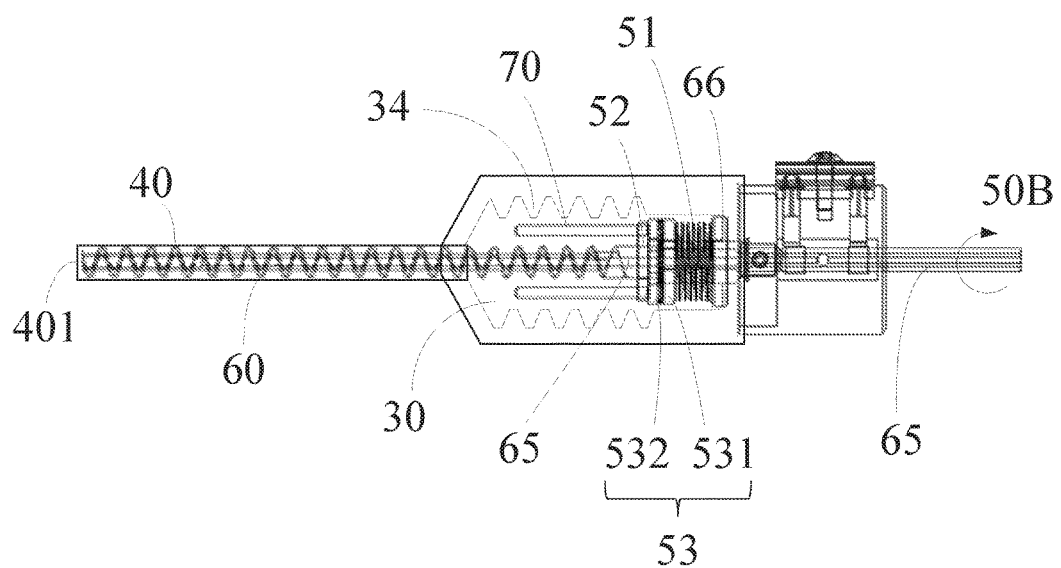

Please refer to FIG. 2D. According to another preferred embodiment, in addition to using the clutch 53 of the driving device 50 to prevent excessively accumulated repairing material from pushing the repairing material towards the exterior tube 40, the injection device according to the present invention further includes inner threads 34 inside the chamber 30 and the push-and-block member 52 screws to the inner threads 34. When the repairing material inside the chamber 30 is loose, the spring 51 will push the transmission lid 531 and the transmission plate 532 to combine tightly. At this time, the driving force given by the spinning shaft 65 will be transmitted to the transmission plate 532 and the push-and-block member 52 such that the push-and-block member 52 can move along the thread direction of the inner threads 34 and compress the repairing material at a slower rate. This design can control the compression rate of the push-and-block member 52 on the repairing material. In addition, the shape of the inner threads can provide greater friction to the transmission plate 532 attached closely to the push-and-block member 52. Thereby, as the repairing material inside the chamber 30 starts to be firm and tight, the friction generated by the accumulation of the repairing material combines with the greater friction provided by the shape of the inner threads 34. As a result, even the structure of the repairing material is not excessively firm and tight, the generated friction still can be greater than the force applied to the transmission lid 531 by the spring 51. The transmission lid 531 will not rotate and move forward. In addition, the screw rod continues to deliver the repairing material towards the exterior tube 40 until the friction generated by the structure of the repairing material and the friction provided by the shape of the inner threads 34 are smaller than the force applied to the transmission lid 531 by the spring 51. Then the transmission lid 531 will redeliver a driving force to the transmission plate 532 and the push-and-block member 52 and push the repairing material. Consequently, the purpose as shown in FIG. 2C can be achieved. Furthermore, the feeding rate for the repairing material can be controlled effectively and the operation of the mechanism can be maintained smoothly.

The driving device 50 and the related components provided in FIGS. 2B and 2C are devices for providing preferred efficiency. Nonetheless, the present invention is not limited to the embodiment. On the contrary, the driving device 50 and the related components can include any or a combination of the above components for achieving the purpose of providing the driving force for the repairing material.

Please refer to FIGS. 2B and 2C. The chamber 30 can further include one or more stirrer 70 disposed and fixed to the driving sleeve 66 on the screw rod 60. When the screw rod 60 spins by a driving force, the driving sleeve 66 disposed thereon will be driven to spin accordingly. At this time, the stirrer 70 spins around the screw rod 60 at the same location and thus achieving the purpose of mixing the powdered repairing material inside the chamber 30. The stirrer 70 also limits the movement of the repairing material and avoids the accumulation of the repairing material on the inner sidewall of the chamber 30 during the spinning process. Based on the above properties, according to a preferred embodiment, the stirrer 70 is stick- or leaf-shaped, as the device 71 shown in FIG. 3. Nonetheless, the present invention is not limited to the embodiment. Contrarily, the shape and quantity of the stirrer 70 can be adjusted according to practical applications.

Figure 3:
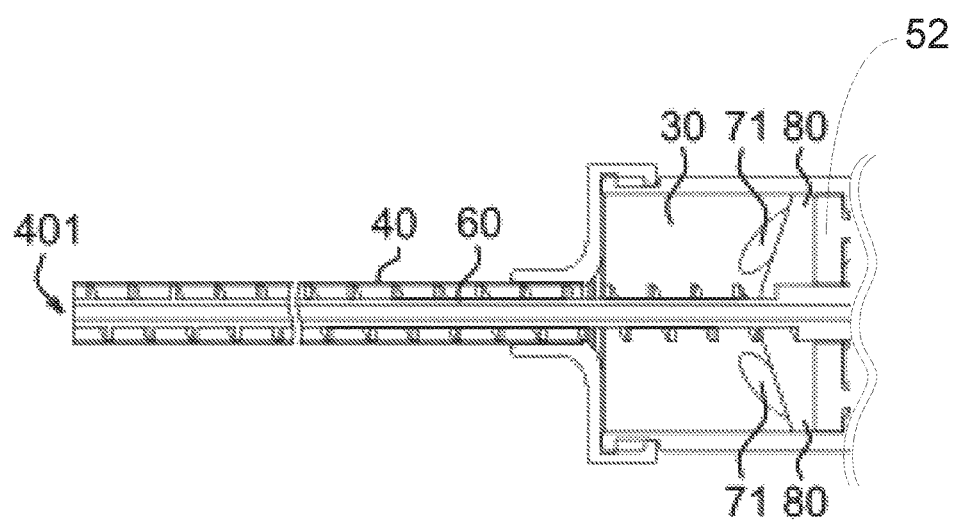
FIG. 3 shows a partial cross-sectional view of the injection device according to another embodiment of the present invention.

Please refer to FIG. 3, which shows a partial cross-sectional view of the injection device according to another embodiment of the present invention. According to the present embodiment, the injection device according to the present invention further comprises a pushing member 80 disposed on the screw rod 60 inside the chamber 30. The pushing member 80 is a cone-shaped projective structure projecting towards the direction the exterior tube 40 and attached to one side of the push-and-block member 52. By the pushing of the pushing member 80, the repairing material can be moved forwards continuously and carried closely on the threads of the screw rod 60, and thus increasing the delivering efficiency of the repairing material by the threads 60. Thereby, the screw rod 60 can output the repairing material uninterruptedly. For example, when the repairing material is a bone cement, the injection device still can convey the bone cement even in the sticky condition. In addition, the pushing force generated by the pushing member 80 and the screw rod 60 enables the bone cement to enter the voids where bones have defects and thus achieving the function of stabilizing the collapsing bones. If the repairing material is an artificial bone, the pushing member 80 enables the material to enter the screw rod 60 continuously. It also presses the artificial bones in bone defects until the bone defects are filled by artificial bones. Compared with the funnel and stick structure according to the prior art, the pushing member 80 and the screw rod 60 according to the present invention can increase substantially the filling quantity of bone defects.

Please refer to FIG. 4A, which shows a partially enlarged view of the screw rod 60 according an embodiment of the present invention. The screw rod 60 is a screw rod having an internal space. It includes a heating part 601, a power supply part 602, and two wires 603, 604. In addition, an output 401 is disposed at one end of the screw rod 60. The heating part 601 can be disposed in the chamber 30, the exterior tube 40, or in both. The power supply part 602 is disposed inside the body 10. The two wires 603, 604 are used for connected the power supply part 602 and the heating part 601 for supplying the electric power required by the heating part 601 for performing electrothermal heating.

The heating part 601 can be formed by, but not limited to, thermistors having a positive temperature coefficient (PTC). The thermistors can heat rapidly. In addition, the temperature can be controlled stably within a certain temperature range; long-term heating does not induce safety concerns; and the connection is easy. Based on the above properties, the heating part 601 according to the present invention can further include semiconductive ceramics containing barium titanate ($BaTiO_3$) or other materials having approximate properties.

Furthermore, the heating temperature of the heating part 601 can be adjusted according to the material properties of different repairing materials. The heating temperature can be set between the glass transition temperature (Tg) and the melting point of a repairing material. By using the above design, high-temperature and long-term heating on repairing materials can be avoided. High-temperature and long-term heating will result in pyrolysis and then lead to fracture of molecules. If this happens, the properties of a material will be completely different. When the heating temperature id controlled between Tg and the melting point, the repairing materials will be softened and transformed only, no excessive expansion will occur. Given the smaller changes in material properties, the injection and repairing processes of repairing materials will be more stable.

Based on the above properties, according to a preferred embodiment, the heating temperature provided by the heating part 601 according to the present invention can be between 50° C. and 260° C. and adjustable according to the properties of the repairing material. For example, when the repairing material is a PLGA-based material, the heating temperature of the heating part 601 can be between 160° C. and 200° C.; when the repairing material is a polycaprolactone-based material, the heating temperature of the heating part 601 can be between 70° C. and 120° C.

There is no limitation on the zone length L of the heating part 601 and the distance D to the outlet 401. Namely, when the heating part 601 is disposed in the chamber 30, the exterior tube 40, or in the both, the zone length L of the heating part 601 can be located at the front end of the screw rod 60 and close to the outlet 401 for heating the repairing material. Alternatively, the zone length L of the heating part 601 can be almost the length of the screw rod 60, so that the heating part 601 is located at the front end of the screw rod 60 as well as at the central part or rear end of the screw rod 60 for heating the repairing material at a plurality of zones. Nonetheless, as described above, because the heating temperature for the repairing material is set between Tg and the melting point, it is not necessary to heat the repairing material to the completely molten phase before it can be moved b the screw rod 60 towards the outlet 401. Based on the above property, according to a preferred embodiment, the zone length L of the heating part 601 according to the present invention is 1 to 15 centimeters, and the distance D between the heating part 601 and the outlet 401 is 0 to 5 centimeters. By using the design, no excessively high heating temperature is required when the heating part 601 is very close to the affected part of an organism. The repairing material still can be softened and transformed with minimum changes in its properties and then be injected into the affected part. Besides, the heating time can be reduced effectively, so that the time the repairing material passing through the heating part 601 can be controlled in, for example, 2 to 3 seconds.

The power supplied to the heating part 601 can an independent AC power supply. Alternatively, it can share a common power system with the external devices connected with the driving device 50, such as the motor or the external electric drill. According to a preferred embodiment, the operating voltage of the heating part 601 can be, for example, a 110V-240V AC power supply or a 12V-36V DC power supply. The heating temperature is set between 50° C. and 260° C. Besides, the shape and size of the heating part 601 can be adjusted according to the design of the screw rod 60.

As shown in FIG. 4A, according to a preferred embodiment, the power supply part 602 contained in the screw rod 60 can further include two copper rings 605, 606. The two wires 603, 604 can be connected to the two copper rings 605, 606, respectively, such that the wires 603, 604 will not wind and be pulled apart as the screw rod 60 spins. The power source for supplying electric power to the copper rings 605, 606 is connected to a stationary external component (not shown in the figure), which can include two copper brushes. The copper brushes can be copper wires or copper plates. The shape of the copper brushes can be arbitrary. The copper brushes are used for contacting the copper rings 605, 606 at the rear end of the screw rod 60 and supplying electricity. For example, the copper brushes can be U-shaped. The copper rings 605, 606 can contact both edges of the brushes. Once the contact at the one edge is bad, electricity still can be supplied through the other. Nonetheless, the structure of the power supply part 602 and the method for supplying power to the heating part 601 are not limited to the above embodiment. That is to say, the structure of the power supply part 602 can be modified according to the different methods for supplying power to the heating part 601.

Please refer to FIGS. 4B to 4E, which show partially enlarged views of the screw rods 61~64 according to another embodiment of the present invention. The screw rods 61~64 can replace the screw rod 60 and be applied to the injection device shown in FIGS. 1 to 3.

Please refer to FIG. 4B. The screw rod 61 includes a first region 61-1, a second region 61-2, a third region 61-3, and a heating part 601. The first region 61-1 is located at the front end of the screw rod 61 and close to the outlet 401. The second region 61-2 is located inside the chamber 30. The third region 61-3 is located between the first region 61-1 and the second region 61-2. The heating part 601 can be disposed in a single region of the screw rod 61. Alternatively, it can be disposed in the first, second, and third regions 61-1, 61-2, 61-3 of the screw rod 61 concurrently. According to a preferred embodiment, the heating part 601 is located in the first region 61-2 of the screw rod 61. Nonetheless, the present invention is not limited to the embodiment.

In the three regions of the screw rod 61, the thread spacings are defined, respectively. The thread spacing in the first region 61-1 is S1; the thread spacing in the second region 61-2 is S2; and the thread spacing in the third region 61-3 is S3. There is no limitation on the three thread spacings S1, S2, S3. They can be identical; they can be totally different; or two of them can be identical and the rest one is different from the two. According to a preferred embodiment, the thread spacing S1 in the first region 61-1 is smaller than the thread spacing S2 in the second region 61-2 and the thread spacing S3 in the third region 61-3; and the thread spacing S2 in the second region 61-2 and the thread spacing S3 in the third region 61-3 are identical. For example, the thread spacing S1 in the first region 61-1 is 4 millimeters, and the thread spacing S2 in the second region 61-2 and the thread spacing S3 in the third region 61-3 are both 8 millimeters. Nonetheless, the present invention is not limited to the example.

Figure 4C:
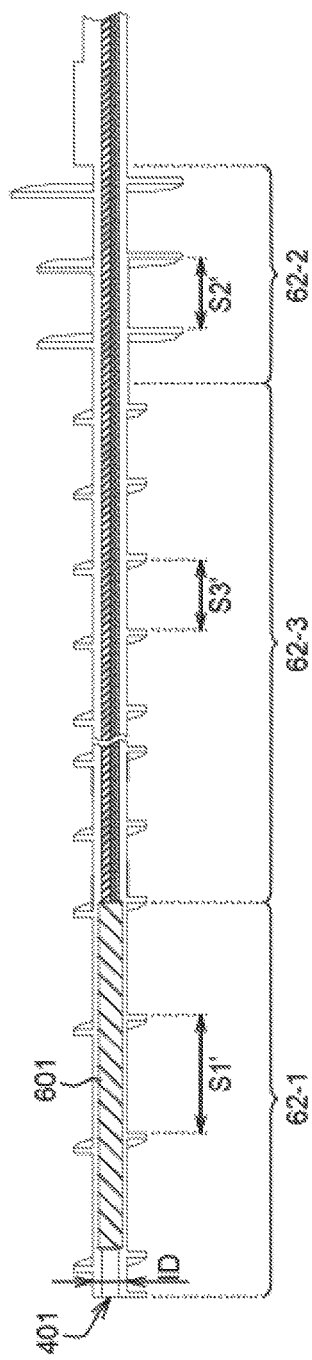
FIG. 4C shows a partially enlarged view of the screw rod according to another embodiment of the present invention.

Please refer to FIG. 4C, which shows a partially enlarged view of the screw rod 62 according to another embodiment of the present invention. The thread spacing S1' in the first region 61-1 is greater than the thread spacing S2' in the second region 61-2 and the thread spacing S3' in the third region 61-3; and the thread spacing S2' in the second region 61-2 and the thread spacing S3' in the third region 61-3 are identical. For example, the thread spacing S1' in the first region 61-1 is 8 millimeters, and the thread spacing S2' in the second region 61-2 and the thread spacing S3' in the third region 61-3 are both 4 millimeters. Nonetheless, the present invention is not limited to the example.

As shown in FIG. 4B, the thread heights in the three regions of the screw rod 61 are defined, respectively. The thread height is defined as the distance between the shaft center of the screw rod 61 and the maximum diameter of the thread, including the thread height H1 in the first region 61-1, the thread height H21 in the second region 61-2, and the thread height H3 in the third region 61-3. According to a preferred embodiment, the thread height H21 in the second region 61-2 is greater than the thread height H1 in the first region 61-1 and the thread height H3 in the third region 61-3. In addition, the thread height H1 in the first region 61-1 and the thread height H3 in the third region 61-3 are identical. For example, the thread height H21 in the second region 61-2 is 13.5 millimeters, and the thread height H1 in the first region 61-1 and the thread height H3 in the third region 61-3 are both 3 or 4 millimeters. Nonetheless, the present invention is not limited to the example.

Regarding to the design of the thread height of the screw rod 61, two or more distinct thread heights can be disposed in a single region. According to a preferred embodiment, two different thread heights H21, H22 can be included in the second region 61-2. The thread height H21 is smaller than the thread height H22. Besides, the thread heights H21, H22 are both greater than the thread height H3 in the third region 61-3 and the thread height H1 in the first region 61-1. Nonetheless, the present invention is not limited to the example. The thread height in respective region of the screw rod 61 can be adjusted according to the shape and size of the exterior tube 40 or the chamber 30.

Moreover, the region lengths of the three regions of the screw rod 61 are defined, respectively, including the region length L1 in the first region 61-1, the region length L2 in the second region 61-2, and the region length L3 in the third region 61-3. According to a preferred embodiment, because the heating part 601 is disposed in the first region 61-1 of the screw rod 61, the region length L2 of the first region 61-1 is adjusted and defined according to the length L of the heating part 601. The region length L2 of the second region 61-2 can be twice to four time the thread spacing S2. The region length L3 of the third region 61-3 can be greater than the region length L1 of the first region 61-1 and the region length L2 of the second region 61-2 of the screw rod 61.

Furthermore, the inner diameters of screw rod in the three regions of the screw rod 61 are defined, respectively, including the screw-rod inner diameter ID1 in the first region 61-1 (not labeled in FIG. 4B; refer to FIG. 4D), the screw-rod inner diameter ID2 in the second region 61-2, and the screw-rod inner diameter ID3 in the third region 61-3. The screw-rod inner diameter is defined as the length of the diameter of a screw rod minus the diameter of the thread. According to a preferred embodiment, as shown in FIG. 4B of the present invention, the screw-rod inner diameter (ID) in the first region 61-1, the screw-rod inner diameter in the second region 61-2, and the screw-rod inner diameter in the third region 61-3 are identical.

Figure 4D:
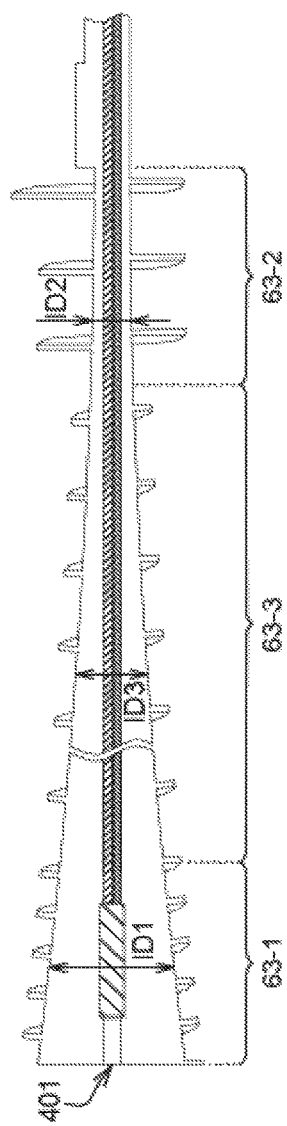
FIG. 4D shows a partially enlarged view of the screw rod according an embodiment of the present invention.

Please refer to FIG. 4D, which shows a partially enlarged view of the screw rod 63 according to another embodiment of the present invention. According to another preferred embodiment of the present invention, a screw-rod inner diameter ID1 in a first region 63-1 of the screw rod 63, a screw-rod inner diameter ID2 in a second region 63-2 of the screw rod 63, and a screw-rod inner diameter ID3 in a third region 63-3 of the screw rod 63 are not identical. In addition, they are variable values such that the screw-rod inner diameters of the screw rod 63 shrink gradually in the direction from the outlet 401 to the chamber 30 and forming a cone-shaped screw rod. For example, the screw-rod inner diameter ID1 in the first region 63-1 can be between 4.1 and 4.3 millimeters; the screw-rod inner diameter ID3 in the third region 63-3 can be between 3.3 and 4.1 millimeters; and the screw-rod inner diameter ID2 in the second region 63-2 can be between 3.0 and 3.3 millimeters. Nonetheless, the present invention is not limited to the example.

Figure 4E:
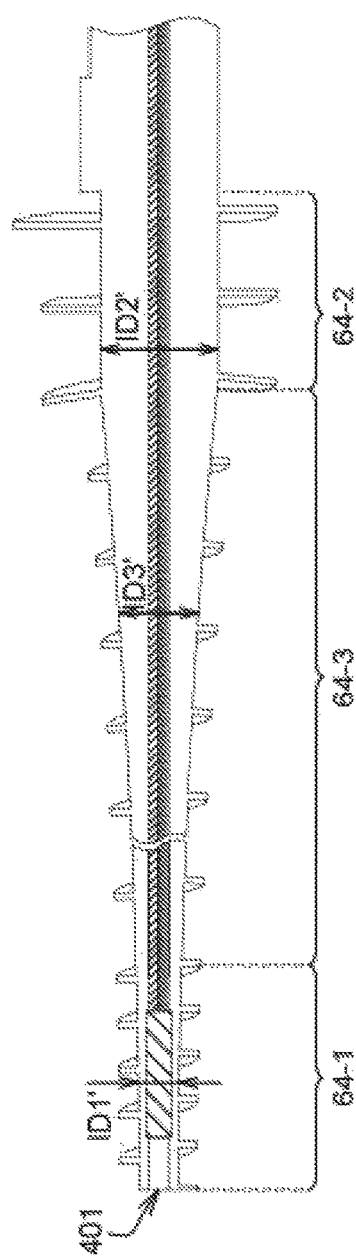
FIG. 4E shows a partially enlarged view of the screw rod according to another embodiment of the present invention.

Please refer to FIG. 4E, which shows a partially enlarged view of the screw rod 64 according to another embodiment of the present invention. A screw-rod inner diameter ID1' in a first region 64-1 of the screw rod 64, a screw-rod inner diameter ID2' in a second region 64-2 of the screw rod 64, and a screw-rod inner diameter ID3' in a third region 64-3 of the screw rod 64 are not identical. In addition, they are variable values such that the screw-rod inner diameters of the screw rod 64 shrink gradually in the direction from the outlet 401 to the chamber 30 and forming a cone-shaped screw rod. For example, the screw-rod inner diameter ID1' in the first region 64-1 can be between 3.5 and 4.0 millimeters; the screw-rod inner diameter ID3' in the third region 64-3 can be between 4.0 and 6.0 millimeters; and the screw-rod inner diameter ID2' in the second region 64-2 can be 6.0 millimeters. Nonetheless, the present invention is not limited to the example.

To sum up, the injection device provided by the present invention can truly convert the circular motion driven by rotation to linear motion by using the design of placing the screw rod inside the exterior tube. By converting the smaller spinning force to a greater forward force, stable and easy-to-operate delivery can be achieved. Thereby, repairing materials can be delivered with ease. In addition, by using the design of the heater at a zone of the screw rod, heating can be performed at the same time when the repairing material is being injected. By heating and injecting the repairing material concurrently, the repairing material can be injected directly in the semi-molten or solid phase. This can avoid changes in material properties caused by heating the repairing material to the liquid phase. In addition, it also improves the flexibility of a surgery by not limited by the coagulation time of the repairing material and hence enhancing the efficiency of the surgery. Thereby, the present invention indeed provides a novel injection device that can improve the operating level of the relevant technical fields.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. An injection device for biological tissue repair, comprising:
    a body;
    a chamber, connected to said body, used for accommodating a repairing material;
    an exterior tube, connected to said chamber, and having an outlet at one end of said exterior tube: and
    a screw rod, disposed inside said chamber and said exterior tube, including threads for dispersing said repairing material, and delivering and outputting said repairing material by using said threads of said screw rod and a driving force coming from a rear end of said screw rod; and
    a driving device for providing said driving force, wherein said screw rod includes a spinning shaft having an end, and said spinning shaft is driven by said driving device and rotates said screw rod accordingly;

wherein said driving device further includes a spring and a push-and-block member disposed at a segment of said spinning shaft inside said chamber and attached to the interface between said body and said chamber; said driving device further includes a clutch at a segment of said spinning shaft and located between said spring and said push-and-block member.

2. The injection device for biological tissue repair of claim 1, wherein said screw rod comprises a heating part for heating said repairing material.

3. The injection device for biological tissue repair of claim 2, wherein said heating part is disposed inside said exterior tube, inside said chamber, or inside both.

4. The injection device for biological tissue repair of claim 2, and further comprising an insulating part disposed between said exterior tube and said screw rod or attached to the inner sidewall or outer sidewall of said exterior tube.

5. The injection device for biological tissue repair of claim 2, wherein said screw rod includes an internal space for disposing said heating part; said heating part is connected to two wires; said two wires are connected to a power supply part and disposed in said internal space; said screw rod includes one or more outlet at one end; and said power supply part is disposed inside said body.

6. The injection device for biological tissue repair of claim 2, wherein said screw rod includes a first region, a second region, and a third region; said first region is located at a front end of said screw rod; said second region is located in said chamber; said third region is located between said first region and said second region; and said heating part is located in said first region.

7. The injection device for biological tissue repair of claim 2, wherein said heating part is a thermistor having a positive temperature coefficient.

8. The injection device for biological tissue repair of claim 7, wherein said heating part is fabricated by semiconductive ceramics containing barium titanate.

9. The injection device for biological tissue repair of claim 1, wherein said chamber is connected to said body by screwing or wedging.

10. The injection device for biological tissue repair of claim 1, wherein said chamber includes an inlet for feeding said repairing material and a cover.

11. The injection device for biological tissue repair of claim 1, wherein said repairing material is powdered, granular, or sticky; and the gradients of said repairing material is selected from the group consisting of thermoplastic biologically-compatible polymers, a calcium biologically-compatible salt, bone cement materials and combinations thereof.

12. The injection device for biological tissue repair of claim 11, wherein said thermoplastic biologically-compatible polymers include poly(glycolic acid), poly(L-lactic acid), poly(D, L-lactic acid), poly(D, L-lactic-co-glycolic) acid (PLGA), or polycaprolactone.

13. The injection device for biological tissue repair of claim 11, wherein said calcium biologically-compatible salt includes hydroxyapatite, tricalcium phosphate, calcium sulfate, dicalcium pyrophosphate, or tetracalcium phosphate.

14. The injection device for biological tissue repair of claim 1, wherein said driving device at least includes a motor disposed inside said body or being a connected electric drill outside said body.

15. The injection device for biological tissue repair of claim 1, wherein said body is further connected to a holding part; said holding part includes one or more motor switch connected with said driving device; and the inside of said holding part is used for disposing said motor.

16. The injection device for biological tissue repair of claim 1, and further comprising a power switch and a power indicator outside said body.

17. The injection device for biological tissue repair of claim 1, wherein said clutch includes a transmission lid and a transmission plate; said transmission lid is attached tightly to said spring; said transmission lid spins along with said spinning shaft; and said transmission plate is attached to said push-and-block member.

18. The injection device for biological tissue repair of claim 1, wherein said chamber includes inner threads screwing to said push-and-block member.

19. The injection device for biological tissue repair of claim 1, wherein said chamber further includes one or more stirrer; a driving sleeve is located at the interface between said body and said chamber; and said stirrer is disposed and fixed at said driving sleeve.

20. The injection device for biological tissue repair of claim 19, wherein said stirrer is stick- or leaf-shaped.

21. An injection device for biological tissue repair, comprising:
a body;
a chamber, connected to said body, used for accommodating a repairing material;
an exterior tube, connected to said chamber, and having an outlet at one end of said exterior tube:
a screw rod, disposed inside said chamber and said exterior tube, including threads for dispersing said repairing material, and delivering and outputting said repairing material by using said threads of said screw rod and a driving force coming from the a rear end of said screw rod; and
a driving device for providing said driving force, wherein said screw rod includes a spinning shaft having an end, and said spinning shaft is driven by said driving device and rotates said screw rod accordingly;
wherein said driving device further includes a spring and a push-and-block member disposed at a segment of said spinning shaft inside said chamber and attached to the interface between said body and said chamber; said screw rod inside said chamber includes a pushing member; and said pushing member is a cone-shaped projective structure projecting towards the direction said exterior tube and attached to said push-and-block member.

22. An injection device for biological tissue repair, comprising:
a body;
a chamber, connected to said body, used for accommodating a repairing material;
an exterior tube, connected to said chamber, and having an outlet at one end of said exterior tube; and
a screw rod, disposed inside said chamber and said exterior tube, including threads for dispersing said repairing material, and delivering and outputting said repairing material by using said threads of said screw rod and a driving force coming from the a rear end of said screw rod;
wherein said screw rod comprises a heating part for heating said repairing material;
wherein said screw rod includes an internal space for disposing said heating part; said heating part is connected to two wires; said two wires are connected to a power supply part and disposed in said internal space; said screw rod includes one or more outlet at one end;

and said power supply part is disposed inside said body; wherein said power supply part further includes two copper rings connected to said two wires, respectively, and to two stationary copper brushes, respectively; and said copper brushes are copper wires or copper plates.

\* \* \* \* \*